United States Patent [19]

Starr

[11] 4,246,100

[45] Jan. 20, 1981

[54] COMPOSITION AND METHOD FOR THE TREATMENT OF SEWAGE

[75] Inventor: Jerry Starr, Holtville, Calif.

[73] Assignee: Bio-Humus, Inc., Holtville, Calif.

[21] Appl. No.: 86,934

[22] Filed: Oct. 22, 1979

[51] Int. Cl.³ .............................................. C02F 3/00
[52] U.S. Cl. ................................... 210/610; 210/916; 210/631; 252/180; 210/749
[58] Field of Search .................. 210/10, 11, 15, 2, 18, 210/59, 64; 252/180

[56] References Cited

U.S. PATENT DOCUMENTS

| | | | |
|---|---|---|---|
| 3,227,648 | 1/1966 | Hahn et al. | 210/11 |
| 3,362,905 | 1/1968 | Gleave | 210/11 |
| 3,558,434 | 1/1971 | Herschler | 210/15 |
| 3,855,121 | 12/1974 | Gough | 210/11 |

FOREIGN PATENT DOCUMENTS 52-12766  1/1977  Japan .......................................... 210/10

*Primary Examiner*—Benoit Castel
*Attorney, Agent, or Firm*—Brown & Martin

[57] ABSTRACT

Sewage treatment composition formed by combination of triancontanol with an organic soil improvement agent derived by digestion of milch cow excrement; and method of treating sewage to reduce sludge by addition of the composition to the sewage.

8 Claims, No Drawings

COMPOSITION AND METHOD FOR THE TREATMENT OF SEWAGE

FIELD OF THE INVENTION

This invention relates to the treatment of sewage to improve its condition for disposal and to a composition for use in that treatment.

BACKGROUND OF THE INVENTION

Disposal of sewage containing human or animal excrement through discharge into septic tanks, settling ponds or cess pools is complicated by the presence of sludge from fecal matter which slows or even blocks the disposal of liquid components by percolation and is objectionable in the use of the sewage for such agricultural purposes as irrigation. While some reduction of sludge occurs through the action of microorganisms present or added to tanks, ponds, or pools, the process is slower than is desired and generates noxious odors including hydrogen sulfide.

OBJECT OF THE INVENTION

It is an object of the present invention to provide a treating agent and method of treatment for sewage using that agent which is effective to give a high rate of sludge reduction and to minimize the development of noxious odors in sewage.

BRIEF STATEMENT OF THE INVENTION

The sewage treatment composition of the present invention is a combination of triacontanol and an organic soil treating agent derived from milking shed wastes. Addition of the composition to sewage according to the present method has been found effectively to reduce sludge and development of noxious odors.

DETAILED DESCRIPTION

I have found that the addition of a very small percentage of triacontanol profoundly alters the properties of a proprietary material whose only known use was as a soil treating agent for agricultural use, particularly to prevent or retard build-up of salts from irrigation water. Surprisingly, the addition has been found to destroy or reduce the effectiveness of the proprietary material for soil treatment, but to form a composition having an unexpected ability to reduce sludge and to facilitate disposal of liquid components by percolation or otherwise to sewage containing animal or human exrement.

The proprietary material for modification by triacontanol is sold as "Biohumus" and is described as an almost water white, thin liquid product obtained by a first digestion of milch cow excrement with yeast under mildly acid conditions and at least one further digestion of the liquid separated from the first digestion products by the action of algae and solar radiation.

Extremely small amounts of triacontanol are effective to impart the new sludge reducing ability to the material. Thus useful results are obtained with as little as about 0.1 ppm. of triacontanol based on the weight of the treating agent. There does not appear to be any upper limit on the amount of triacontanol used, but no significant improvement has been observed on amounts over about 5 ppm.

It has also been found that the effectiveness of the treating agent is improved by the addition to the agent of the B vitamins, thiamine, riboflavin and niacin. Amounts as little as about 0.02% to about 0.15% by weight of each of these vitamins, based on the weight of the treating agent, have been found satisfactory and there does not appear to be any upper limit.

For treatment of sewage, the treating agent is simply mixed with the sewage and allowed to act. Treatment of large volumes of sewage, e.g. washings from a milking shed, may involve feeding the treating agent into a stream of the washings at a controlled rate to mix the treating agent with the washings and discharging the mixture into a disposal pond. Supply of the treating agent is cut off when the amount introduced into the disposal pond is sufficient to give the desired results, after which supply of the washings to the pond is continued. The introduction of further washings stirs up the pond and provides further liquids which, it is believed, is useful in maintaining the activity of the treating agent.

Effective sludge reducing action is obtained where as little as 40 ppm. of the mixture are added and a preferred range of addition is from about 40 to about 4000 ppm. of the treating agent based on the weight of the sewage to be treated.

The following examples are given to aid in understanding the invention, but it is to be understood that the invention is not limited to the particular procedures, conditions or materials of the examples:

EXAMPLE I

Treating agent was prepared by mixing 600 mg. of triacontanol, 3000 gallons of the liquid product of digestion of milch cow excrement under mild acid condition and further digestion of liquid portions from the first digestion by the action of algae and solar radiation ("Biohumus", a proprietary product of Biohumus, Inc. of Holtville, Calif.).

The treating agent was added over a period of 24 hours to the stream of liquid product of washdown from a milking shed in which 1400 cows were milked twice a day, and the resulting mixture was discharged into settling pond having an area of 3 acres and a depth ranging from 2 to 4 feet.

The pond initially showed a high concentration of suspended solids and sludge, but the solids had substantially disappeared when the pond was examined after two weeks and again after 4 weeks as shown by the following table.

|  | Initial | 2 weeks | 4 weeks |
| --- | --- | --- | --- |
| BOD mg/l | 19,000 | 1,200 | 370 |
| COD mg/l | 59,780 | 8,964 | 2,488 |
| Total Solids, % | 8.78 | 1.08 | .3315 |
| Suspended Solids, % | 12.31 | 1.21 | .22 |
| Hydrogen Sulfide, mg/l | −0.05 | −0.05 | X |
| Settleable Solids ml/l/hr | 975 | 200 | 48 |

Note: (−) = Less than

The Biochemical Oxygen Demand, BOD, was determined by Method 405.1 (five days, 20 C.) and is an experimental bioassaytype procedure which measures the dissolved oxygen consumed during dark incubation by microbial life while assimilating and oxidizing the organic matter present. The Chemical Oxygen Demand, COD, was determined by Method 410.1 (Titrimetric, Mid Level) and determines the quantity of oxygen required to oxidize the organic matter in a waste sample, under specific conditions of oxidizing agent, temperature and time.

The mechanism by which the treating agent operates to reduce sludge is not clear. The proprietary material itself and its mixture with triacontanol and vitamins have no significant bacteria content so that the mixture of the invention would appear to work through preferential stimulation of desirable aerobic microorganisms present in the sewage. The following Example II provides some indication that the treating agent affects the balance between development of aerobic and development of anaerobic bacteria since in the samples containing the treating agent there is an initial sharp increase in the count of aerobic bacteria without a corresponding increase in anaerobic bacteria over a period of four weeks and only a small falling off in the aerobic bacteria count at the end if six weeks. The foregoing explanation is given as of possible help but it is to be understood that patentability is not based on its correctness.

Example II

A series of samples were prepared, each comprising five pounds of wet manure from a dairy milking shed. The samples were disposed in white translucent pails and mixed with deionized water to a volume of four and one-half gallons.

The samples had a Biochemical Oxygen Demand, "BOD", of 899 mg. per 1. and a Chemical Oxygen Demand, "COD", of 18,426 mg. per 1.

No additions were made to a first sample serving as a control.

A second sample had 17.7 ml. of the digestion product (Biohumus) and 0.025 mg. of triacontanol admixed; and a third sample had 17.7 ml. of the digestive product, 0.025 mg. of triacontanol, 12.5 mg. of thiamine, 6.25 mg. of riboflavin, 12.5 mg. of niacin and 125 mg. of magnesium chloride admixed.

The pails containing the samples were set on a roof for exposure to sunlight which approximated 75% of daylight.

Bacterial counts were made on the samples and results obtained as recorded in the following table:

|  | Initial | 19th Day | 28th Day | 41st Day |
| --- | --- | --- | --- | --- |
| Sample #1 Standard Plate Count, 32 C., per ml. | not run | 1,900,000 | 360,000 | 1,000,000 |
| Coliform per 100 ml. | not run | Less than 10 | Less than 10 | Less than 10 |
| Sample #2 Standard Plate Count, 32 C., per ml. | not run | 5,700,000 | 7,000,000 | 4,600,000 |
| Coliform per 100 ml. | not run | Less than 10 | Less than 10 | Less than 10 |
| Sample #3 Standard Plate Count, 32 C., per ml. | not run | 7,300,000 | 10,000,000 | 6,000,000 |
| Coliform per 100 ml. | not run | 20 | Less than 10 | Less than 10 |

The above results show that the combination of the digestion product and triacontanol very markedly increases the development of aerobic bacteria over the development in the control, but without corresponding increase in coliform bacteria. Also the combination of the digestion product, triacontanol, vitamins and magnesium chloride was even more effective.

The limited fall-off in the plate count at the last observation still leaves the count higher than the control, but does not appear to occur in the full scale operation as in a dairy settling pond where there is a continuing replenishment of water and sewage.

Having described my invention, what I claim is:

1. A composition for addition to sewage to accelerate reduction of sludge to soluble or finely dispersed state and to minimize generation of hydrogen sulfide comprising a mixture of triacontanol and the liquid product of a first digestion of milch cow excrement under mild acid condition and further digestion of liquid portions from the first digestion by the action of algae and solar radiation.

2. A composition as define in claim 1, in which said triacontanol is present in amount of at least 0.1 ppm. based on the weight of said liquid digestion product.

3. A composition as defined in claim 2, comprising B vitamins.

4. A composition as defined in claim 3 in which said triacontanol is present in amount of from about 0.1 ppm. to about 5 ppm. and said B vitamins comprise from about 0.02% to about 0.15% by weight of each of thiamine, riboflavin and niacin based on the weight of said liquid digestion product.

5. A method for the treatment of sewage containing excrement to accelerate reduction of sludge to soluble or finely dispersed state and to minimize generation of hydrogen sulfide comprising mixing with said sewage a treatment agent comprising triacontanol and the liquid product of a first digestion of milch cow excrement under mild acid conditions and further digestion of liquid portions from the first digestion by the action of algae and solar radiation.

6. A method for the treatment of sewage as defined in claim 5, in which at least about 40 ppm. of said treating agent based on the weight of said sewage is added to said sewage.

7. A method for the treatment of sewage as defined in claim 6, in which said treating agent includes B vitamins.

8. A method for the treatment of sewage as defined in claim 7, in which said triacontanol is present in said treating agent in amount of from about 0.1 ppm. to about 5 ppm., based on the weight of said digestion product and said B vitamins comprise from about 0.02% to about 0.15% by weight of each of thiamine, riboflavin and niacin based on the weight of said liquid digestion product.

* * * * *